(12) United States Patent
Arshi et al.

(10) Patent No.: US 11,389,559 B2
(45) Date of Patent: Jul. 19, 2022

(54) WOUND DRESSING OR DERMAL PATCH

(71) Applicant: BSN medical GmbH, Hamburg (DE)

(72) Inventors: Annahit Arshi, Hamburg (DE); Karsten Hemmrich, Meerbusch (DE); Christian Schulze, Tostedt (DE)

(73) Assignee: BSN MEDICAL GMBH, Hamburg (DE)

( * ) Notice: Subject to any disclaimer, the term of this patent is extended or adjusted under 35 U.S.C. 154(b) by 0 days.

(21) Appl. No.: 16/302,415

(22) PCT Filed: May 15, 2017

(86) PCT No.: PCT/EP2017/061587
§ 371 (c)(1),
(2) Date: Nov. 16, 2018

(87) PCT Pub. No.: WO2017/198603
PCT Pub. Date: Nov. 23, 2017

(65) Prior Publication Data
US 2019/0290799 A1    Sep. 26, 2019

(30) Foreign Application Priority Data

May 17, 2016    (EP) .................................. 16169905

(51) Int. Cl.
A61L 15/44    (2006.01)
A61L 15/26    (2006.01)
A61L 15/42    (2006.01)

(52) U.S. Cl.
CPC ............ *A61L 15/44* (2013.01); *A61L 15/26* (2013.01); *A61L 15/42* (2013.01); *A61L 2300/114* (2013.01); *A61L 2300/41* (2013.01); *A61L 2300/608* (2013.01)

(58) Field of Classification Search
None
See application file for complete search history.

(56) References Cited

U.S. PATENT DOCUMENTS 5,994,444 A * 11/1999 Trescony ............. A61L 29/085
524/429
6,706,274 B2 * 3/2004 Herrmann ............. A61K 31/21
424/423

2011/0293584 A1 * 12/2011 De Bruijn ............... A61P 17/02
424/93.7
2015/0238662 A1 * 8/2015 Handa ..................... C08K 5/32
424/78.31
2018/0000980 A1 * 1/2018 Shuler ................... A61K 31/74

FOREIGN PATENT DOCUMENTS

| CN | 101065084 A | 10/2007 | |
| WO | 9613164 A1 | 5/1996 | |
| WO | 2006058318 A2 | 6/2006 | |
| WO | 2006095193 A2 | 9/2006 | |
| WO | WO-2006095193 A2 * | 9/2006 | ............ A61L 15/44 |
| WO | 2009155689 A1 | 12/2009 | |
| WO | 2014052443 A1 | 4/2014 | |

OTHER PUBLICATIONS

International Preliminary Report on Patentability corresponding to the International Application No. PCT/EP2017/061587, dated Dec. 12, 2018.
International Search Report and Written Opinion for corresponding International Application No. PCT/EP2017/061587, dated Aug. 10, 2017.
Modification, Processing and Molding of General Purpose Pla, Xu Ding, University of Science and Technology of China Press, vol. 1, p. 20.
Buchwald, et al. "Initial Clinical Results with the Wiktor Stent: A New Balloon-Expandable Coronary Stent", Clin. Cardiol. 14, 374-379 (1991).
Communication dated Dec. 24, 2021 of the Columbian patent application No. NC2018/0012346.

* cited by examiner

*Primary Examiner* — H. Sarah Park
(74) *Attorney, Agent, or Firm* — Tarolli, Sundheim, Covell & Tummino LLP (57) ABSTRACT

The invention relates to a pharmaceutical composition and in particular a dermal patch or wound dressing comprising an acid-hydrolyzing oligomer and/or polymer and an acid-activated prodrug such that the active principle in the pharmaceutical composition or in the dermal patch or wound dressing is formed from the prodrug under the effect of acid. The invention further relates to a corresponding method for releasing active principles from a pharmaceutical composition.

19 Claims, 4 Drawing Sheets

WOUND DRESSING OR DERMAL PATCH

RELATED APPLICATIONS

The present invention is a U.S. National Stage under 35 USC 371 patent application, claiming priority to Serial No. PCT/EP2017/061587, filed on 15 May 2017; which claims priority of EP 16169905.3, filed on 17 May 2016, the entirety of both of which are incorporated herein by reference.

The present invention relates to a pharmaceutical composition and, in this context specifically to a skin or wound patch, that comprises an acid-hydrolysing oligomer and/or polymer and an acid-activatable prodrug such that the active substance is produced from the prodrug by the action of acid in the pharmaceutical composition and/or in the skin or wound patch. The invention also relates to a corresponding method for the release of active substances from a pharmaceutical composition.

Numerous skin and wound patches for treatment of wounds or skin diseases are known in the prior art. In this context, the skin or wound patches need to meet various requirements that are major challenges for the skin and wound patches since the wounds or skin diseases to be treated differ greatly. Accordingly, referring to strongly exuding wounds such as burn wounds, the fluid leaking from the patch needs to be taken up, though a film of fluid needs to remain on the wound. Moreover, the patch must prevent the ingress of foreign bodies or pathogens into the wound. It must not adhere to the wound or lead to irritative conditions in the covered tissue. New developments provide for the release of medications and/or wound healing-active substances, which are a significant improvement of therapy especially in the case of chronic wounds due to the treatment of the underlying disease. In patches of this kind involving the release of active substances, it is crucial that the active substance is released in controlled manner.

According to EP 0 481 042 A1, an active substance can be released in controlled manner from a skin patch by way of iontophoresis, whereby an active electrode element, an active substance-containing carrier layer, and a hydrogel layer as a skin contact layer are used. A form of application of this type is associated with numerous drawbacks. Accordingly, as an electrically controlled form of application, it is complex in design and expensive in production. Since the extent of the active substance release is a function of sufficient skin contact and constant conductivity, its use is very error-prone.

As an alternative strategy, WO 2009/054006 A2 discloses a wound patch with a scaffold made of a degradable polymer that encapsulates the active substance. The polymer scaffold is destroyed by the hydrolytic degradation, and the active substances released. These systems are complex in production and are suitable for dermatological use only to a certain degree, since the strong degradation of the polymer scaffold required for release usually proceeds only after an extended period of time.

Accordingly, there continues to be a need for new skin and wound patches that release pharmaceutically active substances in controlled manner.

It is therefore the object of the invention to provide a skin or wound patch that is improved with respect to at least one of the drawbacks specified above.

SUMMARY OF THE INVENTION

The object is met according to the invention in that a skin or wound patch comprising the following is provided:

(a) an oligomer and/or polymer, the hydrolysis of which can produce an acidic environment; and
(b) an acid-activatable prodrug;

whereby the acid-activatable prodrug is activatable in the skin or wound patch by the acid produced by hydrolysis.

The medical patch according to the invention combines several decisive advantages as compared to the therapeutic approaches known from the prior art.

It has been evident, surprisingly, that the acid-generating hydrolysis of oligomers or polymers within said skin or wound patch enables the reliable, controlled generation of active substances from an acid-activatable prodrug and the ensuing controlled release of said active substances.

Since this concerns a release system with a modular design with oligomer and polymer on one side and acid-activatable prodrug on the other side, the system can be adapted specifically to the existing requirements through the selection of the corresponding components.

By encapsulating the prodrug in the polymer matrix, the acid-induced generation of active substances can be combined with the degradation-induced release of the prodrug such that novel release profiles can be attained.

Since the skin or wound patch initially contains only the prodrug, but not the active substance itself, premature inadvertent release of the active substance is excluded.

In contrast to the systems containing a degradable polymer matrix, the oligomer or polymer does not necessarily have to act as a structure-generating element, it can therefore be realised through numerous embodiments ranging from particles via films to fibres.

In this embodiment aimed only at the catalytic function of the oligomers and polymers, existing forms of skin or wound patches can be used in advantageous manner, which facilitates rapid and simpler development.

Alternatively, the acid-generating polymer can just as well itself act as a structure-forming element in its embodiment as a fibre or film such that further matrix components can be omitted.

Since oligomers and polymers can be hydrolysed in a broad spectrum of reactions, extremely varying release rates can be realised. Moreover, enzymes, such as lipases or esterases, can be added to increase the rate of hydrolysis even more.

Numerous biocompatible and acid-hydrolysing polymers are known from the prior art, such as, for example, polylactic acid (PLA) or polyglycolic acid (PGA), which a person skilled in the art can use in this context.

It is another advantage of the solution according to the invention that it provides a platform technology provided it can also be applied to other pharmaceutical compositions such as creams, tablets or lozenges.

Due to the highly controlled release, it is possible to produce skin or wound patches that release only very small amounts of the active substance. This is a crucial advantage, in particular, in the case of highly potent active substances. Moreover, this permits the development of a skin or wound patch as a medical device (e.g. as a so-called class III medical device) in as far as this concerns a wound patch, in which the effect is caused primarily by the mechanical or physical properties of the patch.

Since the skin or wound patch is easy to adapt in terms of its size, shape, and material, it can be adapted specifically to the existing treatment requirements.

Accordingly, it can be used as a prodrug in combination with a pH-labile nitrogen monoxide precursor for the release of highly pure NO, which can otherwise be produced only with considerable effort. By this means, there is no need for an external supply of NO.

The patch according to the invention is a medical patch with a simple design and commercial components such that it can not only be produced inexpensively and easily, but is also easy to use in therapeutic applications and has a low susceptibility to errors.

Skin and wound patches produced with the production method afford more freedom with respect to the characteristic parameters and the selection of materials.

The wound patch according to the invention can be used for a broad range of wounds and is well-suited, specifically, for the treatment of chronic wounds. The provision of an acidic pH medium takes place in the patch regardless of the pH value of the wound. Accordingly, for example the pH value of chronic wounds generally is >7 and these wounds can therefore not acidify a wound patch placed on them. However, due to the intrinsic acidification, the wound patch according to the invention can serve its purpose even if the wound environment is alkaline.

The acidification of the wound patch can also lead to the acidification of the wound space. Since a pH value of <6 and in particular a pH between 4 and 5 is associated with a significant reduction of bacteria that are pathogenic to humans, the wound patch according to the invention can thus have an antibacterial effect and elicit an additional beneficial effect.

In summary, the skin or wound patch according to the invention is a form of therapy, in which a pharmaceutical active substance is released from a medical patch in an inexpensive, reliable, and safe process that can be adapted to the individual patient.

Details of the Invention

In the scope of the invention, a skin or wound patch shall be understood to be any sheet-shaped device that can be placed on areas of the body. The process of placing it on in this context shall comprise simple placing on without tight or adhesive contact as well as an at least partial adhesive connection of the patch to the skin. This type of adhesive connection or glued connection is expediently designed as a reversible adhesive connection.

In the scope of the invention, an oligomer shall be understood to be a molecule that is made up of multiple structurally identical or similar units. If the number of units is extensive (>20 units), this is called a polymer.

An oligomer or polymer that can generate an acidic environment by hydrolysis is characterised, according to the invention, in that the products of hydrolysis, taken together, effect an acidification of the existing pH value. Accordingly, the hydrolysis of a polyester leads to a molecule with a free carboxylic acid group and a hydroxyl group such that the released carboxylic acid effects an acidification of the environment. Preferably, it is the polymer backbone that is hydrolysed during the oligomer or polymer hydrolysis. These are then members of the class of the so-called biodegradable polymers or oligomers. However, side chains of the oligomer or polymer can just as well lead to an acidic hydrolysis, e.g. in the form of ester or anhydride side chains.

In the context of the invention, a prodrug shall be understood to be in an active or poorly active pharmaceutical substance that is converted into an active and/or more active substance only through a chemical conversion. The chemical conversion can be a rearrangement, an addition of an atom or molecule to the prodrug or, preferably, a cleavage of the prodrug. According to the invention, the acid-activatable prodrug shall be understood to be a prodrug, in which the chemical conversion to the active substance is initiated by the addition of an acid (as a proton donor according to the definition of Brønsted and Lowry). This means, in particular, that this chemical conversion is initiated only in an acidic environment (pH<7).

In the simplest embodiment, the oligomer or polymer present in the skin or wound patch is hydrolysed by the aqueous fluid (e.g. in the form of the wound exudate) penetrating into the patch.

Expediently, oligomers or polymers with a high sensitivity to hydrolysis are used in this context. Pertinent examples include the cyclical ester-dimers, glycolide and lactide.

If the wound exudate is acidic, the hydrolysis is promoted further in the course of an acid-catalysed hydrolytic reaction (e.g. in the case of anhydrides and esters). Accordingly, e.g. putrid wounds (i.e. wounds infected by putrid bacteria such as Clostridiae) have a strongly acidic pH value that leads to particularly effective hydrolysis of the oligomer or polymer and is therefore associated with an increased release of the active substance.

Moreover, the hydrolysis within the patch can also be initiated or promoted by enzymes taken up from the body. Accordingly, macrophages that are present in inflamed wounds are known to release, e.g., the cholesterol esterase enzyme, which can penetrate into the wound patch together with the wound exudate and can lead to an ester hydrolysis in the patch.

Due to the skin or wound patch according to the invention, the conversion of the prodrug to the active substance takes place already within the skin or wound patch such that the active substance is released by the skin or wound patch. Therefore, the metabolisation in the body that is common in the case of prodrugs is pre-empted by the patch itself.

This allows prodrugs to be used, for the first time, which as such are not well-suited for being taken up into the body, for example because they have poor pharmacokinetics or are toxic.

In a preferred embodiment, the skin or wound patch additionally comprises an inductor and/or catalyst of the oligomer or polymer hydrolysis.

In the scope of the invention, and inductor shall be understood to be water or an aqueous liquid that is needed as an essential reaction partner of the hydrolysis.

In this context, the skin or wound patch according to the invention needs to be designed appropriately such that the water or aqueous fluid gets to contact the oligomers or polymers only when it is being used. This can be assured, for example, by a waterproof outer packaging such that the hydrolysis is initiated by the atmospheric humidity and/or the skin moisture and/or the wound exudate only when the patch is being used.

Alternatively, the water and/or the aqueous fluid within the wound patch can be present in a compartment that is separate from the oligomer or polymer, e.g. in a separate layer of the patch or in encapsulated form.

A catalyst is considered to be any substance that increases the rate of hydrolysis without being consumed in the process. Accordingly, it can initiate the hydrolysis or accelerate a previously initiated hydrolysis. Inorganic or organic substances or biomolecules can serve as catalysts. The simplest catalyst in this context would be the proton and/or hydronium ion that activates the carbonyl group by protonating the carbonyl-0 atom during the hydrolysis of esters or anhydrides, and facilitates a nucleophilic addition of water.

Amongst the biomolecules, in particular enzymes can be used as catalysts in the scope of the invention.

Numerous enzymes for the individual oligomers or polymers to be hydrolysed are available to a person skilled in the art and can be used in accordance with the specific requirements on hand. Referring to oligoesters or polyesters, it is expedient to use an esterase or lipase as the enzyme.

In this context, preferred enzymes are selected from the following: porcine liver esterase or isoforms thereof, acetyl esterase, butyrylcholine esterase, acetylcholine esterase, *Rhyzopus oryzae* esterase, *Bacillus stearothermophilus* esterase, *Saccharomyces cerevisiae* esterase, *Bacillus subtilis* esterase, pectine esterase, proteinase K, porcine pancreas lipase, *Candida rugosa*-Lipase, *Candida antartica* lipase, *Pseudomonas fluorescens* lipase.

Porcine liver esterase (PLE) or a PLE iso-enzyme, such as PLE-2, PLE-3, PLE-4, PLE-5 or PLE-6, are particular preferred in this context.

In an embodiment of the invention, the polymer hydrolysing while producing acid is selected from the group consisting of polyester, polyanhydride, and polyorthoester, whereby a polyester is preferred.

In this context, the aliphatic polyesters are preferred as polyesters and can be subdivided into two classes, which both can be used according to the invention.

The first class consists of the polyhydroxy alkanoates. These polymers are made up of hydroxyalkanoic acids (also called hydroxy fatty acids) HO—R—COOH. Pertinent examples include polyhydroxy lactic acid (polylactide, PLA) or polyhydroxyglycolic acid (polyglycolide, PGA).

The second class of the so-called poly(alkyldicarboxylates) is produced by polycondensation of diols and dicarboxylic acids. Pertinent examples include poly(butylene succinate) or poly(ethylene succinate).

In this context, preferred polyesters are selected from the following: poly(D,L-lactide), poly(D-lactide), poly(L-lactide), poly(D,L-glycolide) (PDLLA), poly(D-glycolide), poly(L-glycolide), poly (lactide-co-glycolide) (PLGA), polyhydroxybutyrate, poly(ε-caprolacton) (PCL), poly(ε-caprolacton-co-glycolide-co-DL-lactide), poly(p-dioxanone) (PPDO), poly(butylene succinate), poly(ethylene succinate) (PES), poly(butylene succinate-co-adipate), poly(trimethylene carbonate), poly(propylene fumarate) (PPF) and other aliphatic polyesters as well as the copolymers thereof including segmented block copolymers made of polyether and polyester segments such as can be obtained, for example, from the conversion of high molecular polyesters with hydroxy-terminated poly(alkylene glycols).

Preferred polyesters in this context include PGA, PLA or PGLA.

Moreover, polyanhydrides can be used as polymers. Polyanhydrides are polymers with the following basic structure:

According to the invention, aliphatic as well as unsaturated, and aromatic polyanhydrides can be used. In this context, preferred poly anhydrides are selected from the group comprising poly(sebacic acid), poly(adipic acid), poly[1,3-bis(p-carboxyphenoxy) propane:sebacic acid), poly(fatty acid dimer:sebacic acid) copolymer p(FAD:SA), poly(glycerolsebacic acid) (PGS), and the compounds disclosed in the following patent documents U.S. Pat. Nos. 4,757,128; 4,997,904; 4,888,176; 4,857,311; and 5,264,540.

Suitable polyanhydrides a commercially available, such as, for example, Gliadel®—a copolymer consisting of 20 mol-% 1,3-bis(p-carboxyphenoxy)-propane) units and 80 mol-% sebacic acid units.

In a further embodiment, polyorthoesters are used as polymers. These polymers have the following basic structure:

The polyorthoesters comprise the four structural classes POE I-IV shown below, which can all be used in the scope of the invention:

In a further embodiment, the polymer can be a polymer with hydrolysable side chains. These are preferably ester or anhydride groups. Examples of said polymers include: Acetylated pectin, acetylated polyethyleneimine or acetylated chitosan. Said polymers are advantageous in that the hydrolysability can be controlled independent of the polymer backbone by the fraction of ester groups (of anhydride groups). Moreover, no endo-hydrolases are needed as enzymes for degradation, but acetyl esterases can be used for acetylated polymers.

It is expedient to use the corresponding short-chain analogues of the polymers specified above as oligomers. One pertinent example is acetic acid anhydride.

In a preferred embodiment, a cyclical oligomer and particularly preferably a cyclical ester or a cyclical anhydride is used. Preferred pertinent examples are glycolide and lactide.

These cyclical oligomers often are particularly sensitive to hydrolysis such that they can generate an acidic environment in sufficient manner even without catalytic support.

The skin or wound patch can just as well be designed appropriately such that the products of hydrolysis are also released in addition to the active substance.

Accordingly, releasing the acid can generate an acidic environment in the area of the wound that is beneficial for wound healing, as the associated reduction of the absolute number of bacteria is an essential therapeutic goal of modern wound management. Accordingly, the growth of most germs that are pathogenic to humans is inhibited at a pH value <6.0, and in particular between pH 4-5, whereby their optimum pH is reported to be 6.2-7.8. Accordingly, it has been shown that the bacterial density is clearly reduced in patients with hemiplegia or diabetes mellitus after the pH value of the intact skin was lowered through the topical application of acidic externals.

This bactericidal effect of the released acid can be supported in beneficial manner through the release of the alcohol as the second reaction product of an ester hydrolysis.

The acid-degradable polymer can take any form known for polymers, meaning that it can be designed as a gel, particle, foil, film, foam or a textile (two-dimensional) structure.

In a preferred embodiment of the invention, the acid-hydrolysing polymer of the skin or wound patch is designed in the form of a fibre or an enveloping layer of a core fibre.

In this context, the core fibre preferably consists of a thermoplastic material that is similar or identical to the acid-degradable polymer forming the enveloping layer in terms of its spinning performance, meaning that the materials are spinning-compatible.

The selection of a suitable fibre cross-section provides a person skilled in the art with an additional option for controlling the degradability of the polymer. Examples to be mentioned include the following fibre cross-sections: flat, oval, round, triangular, trilobate, Y-shaped, T-shaped, M-shaped, S-shaped, H-shaped, star-shaped or snowflake-like.

A person skilled in the art can basically use all processing types known from fibre technology for the processing of the polymer fibres according to the invention, such that the fibre can form the component of a woven fabric, knitted fabric or non-woven fabric.

Said corresponding fibre structures can fully consist of acid-degradable polymer fibres, or mixed structures can be used, which additionally or predominantly contain conventional, i.e. non-acid-hydrolysing, fibres.

In one embodiment, the acid-activatable prodrug can itself be an ester that is converted by the acid into the free carboxylic acid as the active substance.

In a further embodiment, the acid-activatable prodrug is a deprotonated acid ion that is converted by the acid into the non-polar carboxylic acid, which can then penetrate into the skin more easily.

In a preferred embodiment, the acid-activatable prodrug is a pH-labile nitrogen monoxide precursor (NO donor, NOD) that reacts with the acid to produce nitrogen monoxide as the pharmaceutically active substance.

pH-labile NO precursors are known in the prior art and a person skilled in the art would be familiar with them.

In a preferred embodiment of the invention, the pH-labile nitrogen monoxide precursors are selected from the group containing organic nitrates, inorganic nitrates, nitrites, sulfur-, nitrogen- or oxygen-nitroso compounds, NO-metal compounds, and NO-chelating substances.

Examples of pH-labile NODs comprise diazeniumdiolates (e.g. U.S. Pat. Nos. 7,105,502; 7,122,529; 6,673,338), trans[RuCl([15]aneN4)NO]+2+, nitrosyl ligands, 6-nitrobenzo[a]pyrrole, S-nitroso-glutathione, S-nitroso-thiol, nitroaniline derivatives (see US 2013/0224083), 2-methyl-2-nitrosopropane, imidazolyl derivatives, hydroxylnitrosamine, hydroxylamine, and hydroxyurea.

Preferably, the NOD is a pharmacologically tolerable substance.

In a preferred embodiment, the NOD is a nitrite salt. Nitrates of alkali or alkaline earth metals are preferred in this context. To name some examples: $LiNO_2$, $NaNO_2$, $KNO_2$, $RbNO_2$, $CsNO_2$, $FrNO_2$, $Be(NO_2)_3$, $Mg(NO_2)_3$, $Ca(NO_2)_3$, $Sr(NO_2)_3$, $Ba(NO_2)_3$ or $Ra(NO_2)_3$. In this context, the concentration of the nitrite salts, relative to the total weight of the layer(s) containing them, can be up to 20% by weight, preferably between 0.25 and 10% by weight, particularly preferably between 3 and 7.5% by weight.

$NaNO_2$, is particularly preferred as the NOD and, in even more preferred manner, is contained in the medical patch together with ascorbate or ascorbic acid as a radical scavenger system.

In this context, the concentration of the nitrite salts, relative to the total weight of the layer(s) containing them, can be up to 20% by weight, preferably between 0.25 and 10% by weight, particularly preferably between 3 and 7.5% by weight.

In an alternative embodiment, a nitrate salt that is subject to enzymatic conversion to the corresponding nitrite salt can be used just as well. Nitrates of alkali or alkaline earth metals are used preferably in this context. To name some examples: $LiNO_3$, $NaNO_3$, $KNO_3$, $RbNO_3$, $CsNO_3$, $FrNO_3$, $Be(NO_3)_3$, $Mg(NO_3)_3$, $Ca(NO_3)_3$, $Sr(NO_3)_3$, $Ba(NO_3)_3$ or $Ra(NO_3)_3$. In this context, the concentration of the nitrate salts, relative to the total weight of the layer(s) containing them, can be up to 20% by weight, preferably between 0.25 and 10% by weight, particularly preferably between 3 and 7.5% by weight.

In another embodiment of the invention, the NODs can be coupled to a polymer or oligomer. Pertinent methods for coupling of NODs to polymers or disclose, for example, via U.S. Pat. No. 5,405,919. In one embodiment, the NOD-coupled polymer is a polymer that is provided with diazonium diolate groups.

In a special embodiment of the invention, the NODs can be coupled to the acid-hydrolysing polymer or oligomer according to the invention. By this means, the two basic components of the skin or wound patch according to the invention are combined in one substance.

The released amount of NO ranges from 50 to 600 ppm, and preferably from 160 to 400 ppm. Said amounts are therapeutically effective without leading to major adverse effects.

In another embodiment of the invention, the acid-activatable prodrug, and in particular the NOD, is present as micro- or nanoparticles.

These can be embedded in the polymer matrix in a particularly preferred embodiment.

To remove the multiply oxidised nitrogen oxides, oxygen radical anions or hydroxyl radicals that arise during the generation of NO that is preferred according to the invention, it is advantageous for the wound or skin patch to comprise a system, which degrades or neutralises multiply oxidised nitrogen oxides, oxygen radical anions or hydroxyl radicals, whereby the system preferably is selected from the group containing ascorbic acid, vitamin E and derivatives thereof, thiols, and radical scavengers.

The substances used in the radical scavenger system can not only trap the radical side products arising during the generation of NO, but can also make sure that the corresponding layer is oxygen-depleted or even oxygen-free and that, accordingly, any initial reaction of the NO thus generated with the oxygen is prevented.

Expediently, the pH-labile NODs and the radical scavenger system are present in the same layer. By this means, the radicals arising as side products during the acidolysis can be trapped directly, without reacting with further substances to produce possibly toxic substances. Preferably, the NODs and the radical scavenger system are contained in the middle layer.

In an alternative embodiment, for example if the NOD and radical scavenger system are chemically incompatible, these two components are present in different layers. In this context, it is expedient for the NOD to be contained in the middle layer and for the radical scavenger system to be contained in the inner layer, i.e. skin-facing layer, such that the NO generated by acidolysis and its side products are cleaned by the inner layer before they appear on the skin.

In a further embodiment, the skin or would patch comprises coated fibres, in which the enveloping layer of the core fibre contains a radical scavenger system. The radical scavenger molecules provided in the envelope can inactivate toxic side products of the generation of NO before they exit from the fibre. The NOD can be present either in the core fibre or in the enveloping layer in this context. It is particularly preferred for the NOD to be present in the core fibre and for the radical scavenger system to be present in the enveloping layer. This allows incompatible systems to be combined with each other.

The "radical scavenger system" of the preceding embodiments is preferred to be an antioxidant, and particularly preferably is ascorbate or ascorbic acid. A $Cu^{2+}$ compound is also preferred for this purpose, in particular an inorganic $Cu^{2+}$ salt such as $CuCl_2$.

A person skilled in the art is aware of numerous systems that are capable of degrading or neutralising multiply-oxidised nitrogen oxides, oxygen radical anions, hydroxyl radicals, or aqua-complexed electrons. A person skilled in the art will select these according to the corresponding layer composition of the skin or wound patch.

Suitable antioxidants for a lipophilic skin or wound patch layer, such as can be provided by hydrophobic polymers, include tocopherols, tocotrienols, tocomonoenols, Irganox®, Irgafos®, butylhydroxyanisole (BHA) and Butylhydroxytoluene (BHT).

Organic sulfur-containing compounds such as glutathione, cysteine or thiolactic acid or organic acids such as ascorbic acid, alpha-lipoic acid, hydroxycinnamic acids such as p-cumaric acid, ferulic acid, sinapinic acid or caffeic acid, or hydroxybenzoic acids such as gallic acid, protocatechuic acid, syringic acid or vanillic acid are well-suited for a hydrophilic skin or wound patch layer.

Other preferred antioxidants comprise polyphenolic compounds such as anthocyanins, flavonoids and phytoestrogens.

Preferably, the skin or wound patch, and more preferably the prodrug-containing layer, contain one or more of the following additional substances: Catalysts, detergents, buffer substances, chromophores, substances stabilising the prodrug such as, for example, dimethyl sulfoxide or ethanol, substances increasing the half-life of NO such as are disclosed in US 2003/0039697, NOD stabilisers, antioxidants, dyes, pH indicators, care agents, fragrances, pharmacological agents.

In a preferred embodiment, the buffer substance causes the pH value to be maintained in an optimum pH range for the generation of active substance and for the skin environment if the acid production is too intense. Accordingly, it needs to be noted that the acid produced during ester hydrolysis can stimulate further hydrolysis of the ester and can thus include a positive feedback loop. In this context, the buffer substance expediently buffers in a pH range from 4 to 7, preferably from 4.5 to 6, and particularly preferably from 5 to 5.5.

If a pH-labile NO precursor is used as prodrug, for example dimethyl sulfoxide or ethanol can be used as a stabiliser of the NO precursor. Substances that prolong the half-life of NO are disclosed, for example, in US 2003/0039697.

In a further preferred embodiment, the multi-layer skin or wound patch, and preferably the prodrug-containing layer, further contains a crystallisation inhibitor. Various surfactants or amphiphilic substances can be used as crystallisation inhibitors. They should be pharmaceutically acceptable and tested for the use in medications. One particularly preferred example of a crystallisation inhibitor of this type is soluble polyvinyl pyrrolidone, which is commercially available, for example, by the trade name of Kollidon® (Bayer AG). Other suitable crystallisation inhibitors include copolymers of polyvinyl pyrrolidone and vinyl acetate, polyethylene glycol, polypropylene glycol, glycerol and fatty acid esters of glycerol or copolymers of ethylene and vinyl acetate.

Optionally, the skin or wound patch contains a penetration promoter. Said penetration promoters (also referred to as "permeation enhancers") improve the permeation properties for penetration of the pharmacologically active substances into the skin. Examples of penetration promoters include fatty alcohols, fatty acids, fatty acid esters, fatty acid amides, glycerol or glycerol-fatty acid esters, N-methyl pyrrolidone, terpenes such as limonene, α-pinene, α-terpineol, carvone, carveol, limonene oxide, pinene oxide or 1,8-eucalyptol.

A person skilled in the art will select suitable substances or mixtures of substances with a view to the respective purpose and based on the person's general professional knowledge. The person skilled in the art will specifically make sure that physiologically compatible and/or dermatologically compatible substances or mixtures of substances are used for the use as skin or wound patch.

In one embodiment of the invention, the medical patch, and in particular the prodrug-containing layer, contains one or more pharmacologically active substances. These can support the pharmacological effect of NO or act independent of NO in a therapeutically relevant manner considering the respective application.

In one embodiment of the invention, the medical patch contains one or more of the following pharmacologically active substances: anti-inflammatory agents such as, for example, non-steroidal anti-inflammatory drugs (NSAIDs) or corticoids, immunosuppressants, antibiotics, anticoagulants, anti-thrombotic agents, antiviral agents, antifungal agents, local anaesthetics, and analgesics.

In a preferred embodiment, the pharmacologically active substance is present in the form of wax-like particles with a low melting point that melt upon contact with the skin and release the substance.

In a further embodiment, the skin or wound patch, and preferably the NOD-containing layer, is oxygen-depleted or oxygen-free. Accordingly, the oxygen content of the skin or wound patch or of the NOD-containing layer is less than 2%, preferably less than 1.5%, and particularly preferably less than 1%, relative to the concentration of the NOD.

The oxygen depletion or oxygen absence according to the invention can be caused by treatment of the individual components of the skin or wound patch or by supplying gas to intermediate stages or the ready-made skin or wound patch using an inert gas (such as argon or nitrogen). Expediently, a skin or wound patch of this type is to be packaged in gas-tight manner such that the oxygen depletion and/or absence of oxygen is maintained until the time of use.

In a further embodiment, the skin or wound patch, and preferably the NOD-containing layer(s), comprise(s) an oxygen absorber in order to attain the oxygen depletion or absence of oxygen. Suitable oxygen absorbers include: Irganox®, Irgafos®, butylhydroxyanisole, butylhydroxytoluene, ascorbic acid or pyrogallol.

Figure 4:
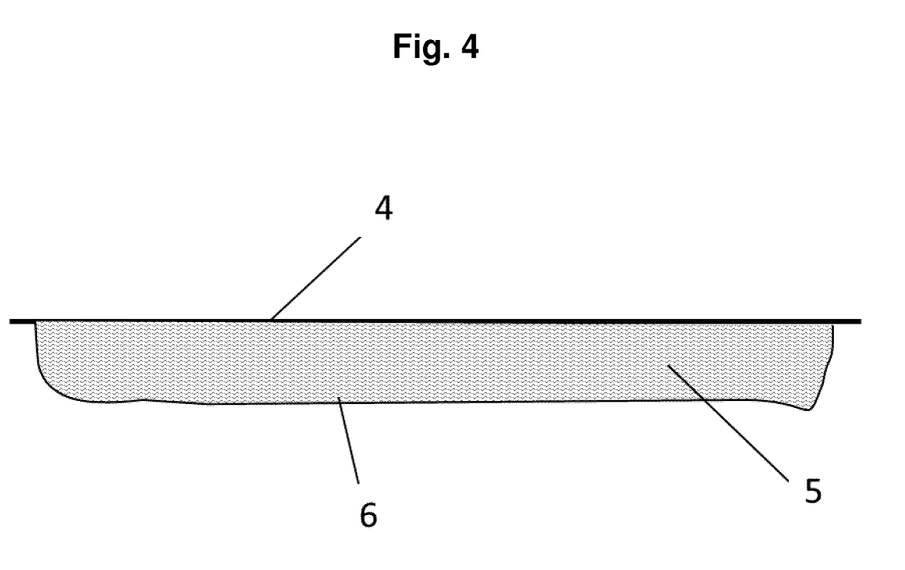
FIG. 4: shows a wound patch according to the invention with a carrier (4) (e.g. as a film or fabric backing) onto which a knitted fabric or non-woven fabric (5) is applied that comprises fibres made of acid-hydrolysing polymers or oligomers and a final protective layer (6) that is permeable to NO and prevents the knitted fabric or non-woven fabric from sticking to the wound.

In a special embodiment, the wound patch comprises a carrier that has a layer made of a knitted fabric or non-woven fabric arranged on it. In this context, the non-woven fabric or knitted fabric comprises fibres that contain the acid-hydrolysing polymer or oligomer. On the side facing the wound, the wound patch is preferably provided with a protective layer that is permeable to NO and prevents the knitted fabric or non-woven fabric from sticking to the wound.

In one embodiment, the multilayer skin or wound patch of the present invention can be obtained by (i) spreading a solution containing NOD and at least one hygroscopic polymer or copolymer on a surface and by drying it, and (ii) laminating, to the layer thus obtained, a further layer as well as a layer, which becomes permeable to NO during the treatment.

In an alternative embodiment, the NOD-containing solution is added onto a non-woven fabric, a knitted fabric or a hygroscopic polymer network in step (i) and dried subsequently to attain an NOD coating of the fibres.

In an embodiment of the invention, the skin or wound patch is designed to be a multi-layered patch that comprises the following layers:
  a carrier layer;
  a layer containing an acid-hydrolysing oligomer or polymer and an acid-activatable prodrug, in particular an NOD; and
  optionally, a backing layer.

Therefore, according to a particular aspect, the invention provides a skin or wound patch that is suitable for use during the treatment of diseases by placing or sticking the patch onto the area to be exposed to it.

Specifically, in this context, the skin or wound patch according to the invention can be used for stimulation of the metabolism of tissues through external application, in dermatology it can be used for treatment of surgical or accident-related wounds, chronic, non-healing and/or poorly healing and/or bacteria- and/or fungi-infested wounds as well as for treatment of dermatological diseases from the realm of inflammatory, immunologically controlled and/or autoimmune diseases. Preferred examples of possible application areas include the following:
  treatment of diabetic feet and wounds;
  treatment of neuropathic pain;
  treatment of varicose veins;
  treatment of local superficial or deep-seated ischaemia and thrombopathic diseases of tissues;
  treatment of acute and chronic inflammations of the skin;
  treatment of skin allergies;
  treatment of parasitic skin infections;
  treatment of atopic dermatitis in particular neurodermitis, dermatomyositis, and pemphigus vulgaris;
  treatment of wound defects, such as chronic diabetic-neuropathic ulcers, crural ulcer, decubital wounds;
  treatment of secondary healing infected wounds;
  treatment of primary healing wounds, such as ablative lacerations or ablative abrasions;
  treatment of extensive body regions for therapy of systemic diseases, e.g. such as elevated blood pressure (hypertension) and related haemodynamic diseases;
  treatment of patients having skin grafts;
  treatment of diabetic pain in the lower extremities (foot or leg); and
  treatment of poorly perfused flap grafts.

Moreover, it may be possible to also address systemic diseases, such as, e.g., elevated blood pressure (hypertension) and related haemodynamic diseases, by treating extensive body areas.

For the purpose of treatment, the skin or wound patch is placed on the area to be exposed and then, preferably, the moisture present in the wound and/or skin initiates the hydrolysis of the acid-hydrolysing polymer or oligomer. The time of treatment can vary from a few minutes to several days.

In an embodiment of the invention, the time of treatment is between 5 min and 3 days, preferably between 5 hours and 2 days, and particularly preferably between 20 and 30 hours.

In an embodiment of the invention, the medical patch is used for treatment of diseases. In this context, it is expedient to place the medical patch onto the body area to be exposed, i.e. for example a section of the trunk or a section of an extremity, and then the respective area is exposed to the NO by the acid-induced release of NO from the skin or wound patch.

In a particularly preferred embodiment, the medical patch according to the invention is used for treatment of chronic lower limb wounds, specifically in diabetics. In this context, the treatment can act in terms of prophylaxis to reduce the risk of chronic wounds arising and to reduce the number of medical amputations. Accordingly, the reduction of the neuropathic leg pain and the establishment of an improved wound environment is associated with a significantly improved quality of life for the patient. Moreover, the reduced period of wound management is expected to lead to a significant reduction of the treatment cost.

In an embodiment of the invention, the medical patch according to the invention is used for treatment of poorly healing wounds. Impaired arterial circulation and/or venous back-flow disorders are significant causes of the development and chronicity of lower limb wounds. NO-related arterial vasodilation improves the blood circulation in the afflicted tissue and the anti-thrombogenic effect of NO significantly promotes and/or facilitates venous back-flow of the blood. The NO-dependent improvement of both haemodynamic parameters is the crucial therapy-relevant aspect of a local or systemic effect that significantly reduces the risk of wound development and/or significantly accelerates wound healing. Accordingly, the NO supplied by the medical patch to the body in a locally restricted form, i.e. to the section of extremity or trunk section to be treated, can be used successfully for treatment of poorly healing wounds.

In a particular embodiment, the medical patch according to the invention is used for treatment of diabetic pain in the lower extremities, i.e. foot and/or leg. Diabetic pain is a very common event in the course of a diabetic disease. Diabetic foot/leg pain is the result of a persistent increase in the blood glucose concentrations, which is the underlying cause of the nerve and vascular damage observed during a diabetic disease. NO-related arterial vasodilation improves the blood circulation in the afflicted tissue and helps through an effect on the conduction of pain such as to reduce the pain. The NO supplied to the foot and/or leg from outside by the medical patch can therefore be used successfully for therapy of diabetic foot or leg pain.

In a special embodiment of the invention, the medical patch according to the invention is used for treatment of patients with (skin) grafts and, in this context, in particular for treatment of poorly perfused flap grafts. The two haemodynamic parameters specified above, i.e. arterial circulation and venous back-flow, are also essential parameters for the therapeutic success of surgical flap grafts. Flap grafts are surgical techniques of plastic surgery, in which skin and/or tissue is transferred from one site (where it is non-essential) to another site of the same individual. Usually, this concerns just skin flaps, but any tissue with or without skin as well as pedicled (i.e. including its respective blood-supplying vessels and nerves) as well as free (i.e. including connection of the blood vessels to the blood supply of the new environment) can be transplanted. The functional acceptance of the transplanted tissue depends exclusively on the arterial blood supply and controlled venous discharge. NO-related arterial vasodilation improves the blood circulation and therefore the needed supply of the flap graft and the anti-thrombogenic effect of NO promotes and facilitates venous back-flow of the blood. Therefore, NO preparations used from outside can assure and/or promote the success of a therapeutic option that is based on flap grafting.

Accordingly, the medical patch according to the invention cannot only be used for treatment of chronic or acute diseases, but also for possible prevention of this type of diseases. Unless specified otherwise, the term "therapy" or "treatment" shall encompass all measures aimed at alleviating, healing or preventing the diseases that are relevant in this context.

A treatment of this type involving the placement of the patch can be applied in intervals of 1, 2, 3, 4, 5, 6 or 7 days or even multiple times daily, whereby changing the patch after 1 to 2 days is preferred.

According to another aspect, the invention provides a pharmaceutical composition for release of a pharmaceutically active substance which comprises the following:
 an oligomer or polymer that can produce acid by means of hydrolysis; and
 an acid-activatable prodrug;
 whereby the acid-activatable prodrug is activatable by the acid produced by hydrolysis.

In a preferred embodiment, the prodrug of the pharmaceutical composition is a pH-labile NO precursor (NOD).

In this context, the pharmaceutical composition can be any and application form comprises, for example, capsule, tablet, film, lozenge, gel, cream, and aerosol.

The embodiments described above for the skin or wound patch (in particular with respect to the NOD and the acid-hydrolysing oligomers and/or polymers) can be used in the pharmaceutical composition according to the invention as well.

In a further aspect, the invention provides a method for releasing an active substance from a pharmaceutical composition, and, in particular for releasing the active substance from a skin or wound patch, whereby the method comprises the following steps:
 (a) providing a pharmaceutical composition and, in particular, a skin or wound patch comprising an oligomer and/or polymer that can produce an acid environment by means of hydrolysis, and an acid-activatable prodrug;
 (b) contacting the polymer and/or oligomer to an inductor or catalyst such that the inductor or catalyst effects at least partial hydrolysis of the oligomer and/or polymer and such that an acidic environment is produced by the products of hydrolysis;
 (c) conversion of the acid-activatable prodrug into an active substance by the acidic environment from step (b);
 (d) release of the active substance from the pharmaceutical composition and, in particular, from the skin or wound patch.

The catalyst or inductor acting in step (b) can be a component of the pharmaceutical composition or can be added externally to said pharmaceutical composition. Accordingly, for example, it can be provided by the organism to be treated.

Moreover, the skin or wound patch can also comprise a device for measuring the blood circulation, which allows the duration of treatment and/or the intensity of treatment to be controlled particularly well based on the therapeutic success. A person skilled in the art is aware of numerous devices for measurement of the blood circulation. Examples include vessel tachometers or the micro-sensor disclosed in WO 97/46853.

Other blood vessel-related measuring parameters, such as the reddening of the skin or the skin temperature, can serve as surrogate parameters for the blood circulation of the skin, for which corresponding measuring methods and devices are known from the prior art.

REFERENCE NUMBERS

1 Fibre made from an acid-hydrolysing polymer
2 Fibre made from an acid-non-hydrolysing polymer
3 NO prodrug particle
4 Carrier layer
5 Knitted fabric or non-woven fabric with fibres containing the acid-hydrolysing polymers
6 NO-permeable protective layer

FIGURES

The invention is illustrated in the following in more detail based on the figures without limiting the invention to the figures shown. In the figures.

EXAMPLES

I. Generation of NO in a Wound Patch by Means of an Acid-Hydrolysing Polymer

1. Materials:
NO gas analysis device Eco physics CLD 822 (ECO PHYSICS AG, Duernten, Switzerland) for quantification of NO
Sodium nitrite (90 mg) and sodium-L-ascorbate (90 mg)
2 ml distilled water
15 cm$^2$ polylactide (PLA) membrane (membrane with micropores with a diameter of 2-50 μm, composition: Polylactide tri-polymer as the main component, trimethylene carbonate and ε-caprolactone (lactocapromer) as ingredients.

2. Method 90 mg sodium-L-ascorbate and 90 mg NaNO$_2$ were distributed evenly on a PLA membrane with a size of 15 cm$^2$.

After the addition of 2 ml distilled water, a nitrogen carrier gas (25 ml/min) was streamed over the membrane in a chamber to feed the outgassing NO to the quantification by CLD.

The NO concentration was quantified continuously for a period of 100 minutes using the CLD system.

3. Results

Figure 1:
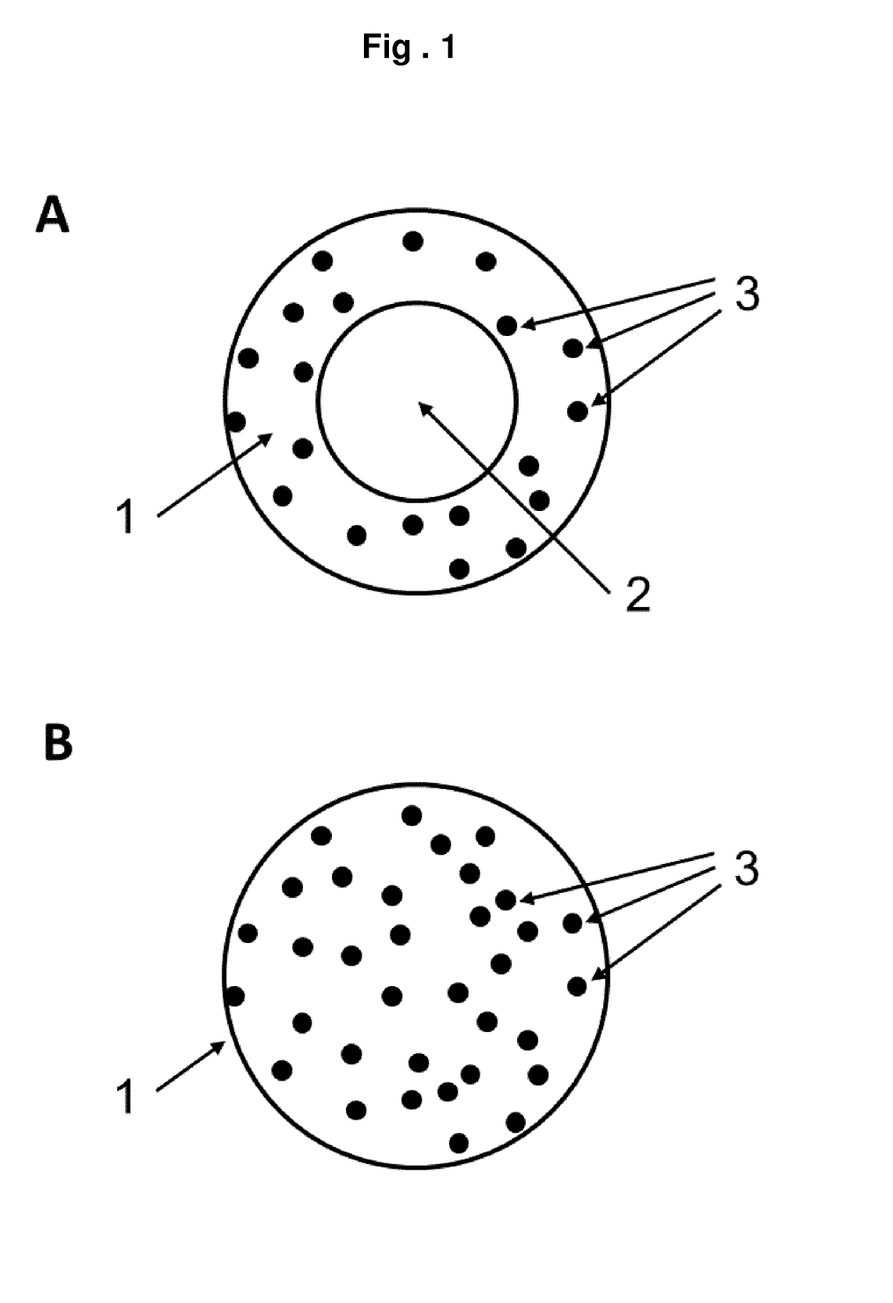
FIG. 1: shows two embodiments of a fibre according to the invention: In (A) with a core fibre made of an acid-non-hydrolysing polymer (2) and a fibre jacket made of an acid-hydrolysing polymer (1) containing NO prodrug particles (3). In (B), a fibre made of an acid-hydrolysing polymer (1) containing NO prodrug particles (3) is shown.
Figure 2:
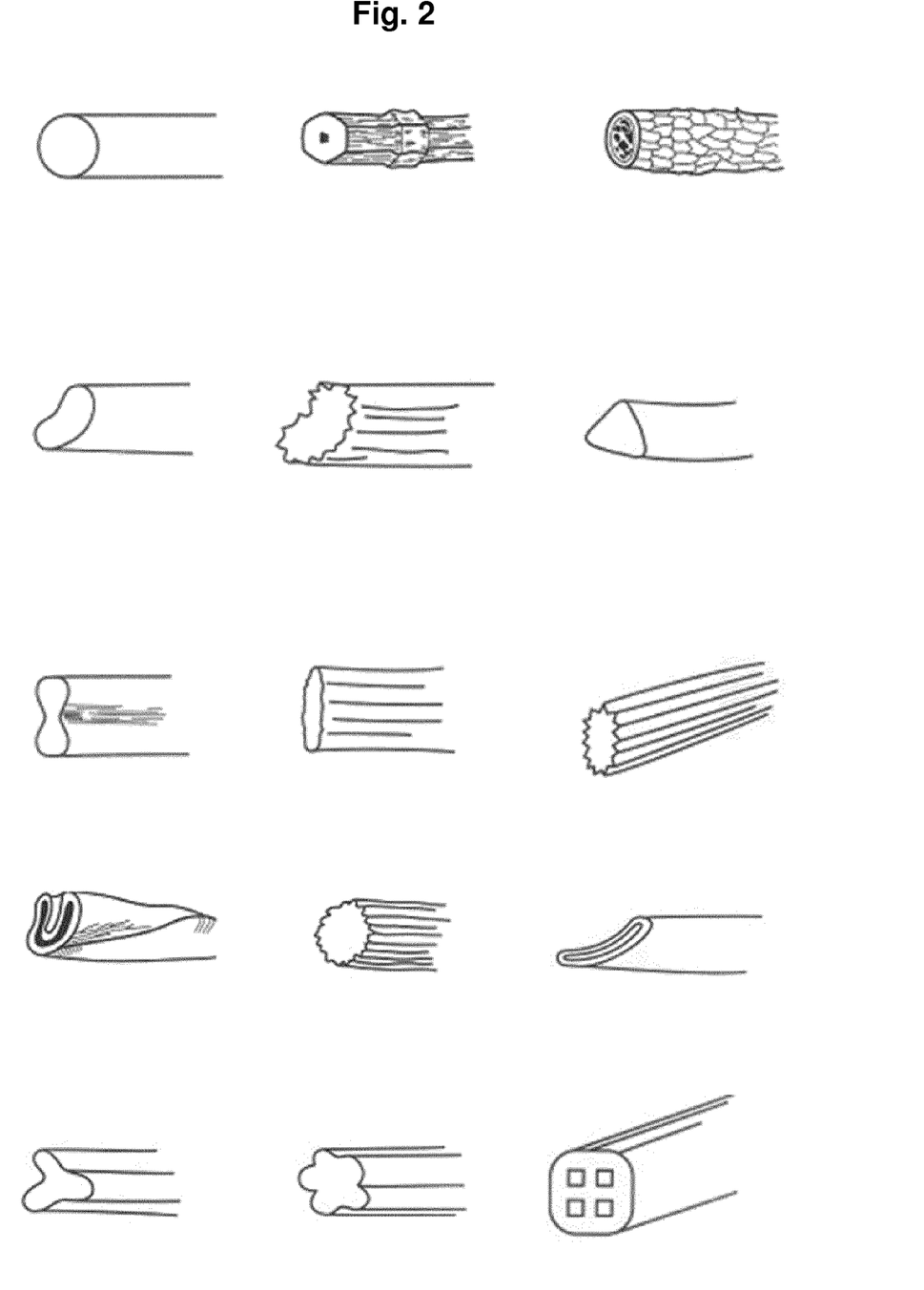
FIG. 2: shows selected cross-sections of a fibre according to the invention. A schematic depiction shows the following in the order from top left to bottom right: Circular with an even diameter; polygonal with lumen; oval to round with overlapping scales, oval-flat with lumen pleating, star-shaped, bean-shaped, serrated bean-shaped, triangular with rounded corners, trilobate, lobular with notches, dumbbell-shaped, flattened, concertina-shaped, collapsed tube with hollow core, rounded square with four hollow spaces.
Figure 3:
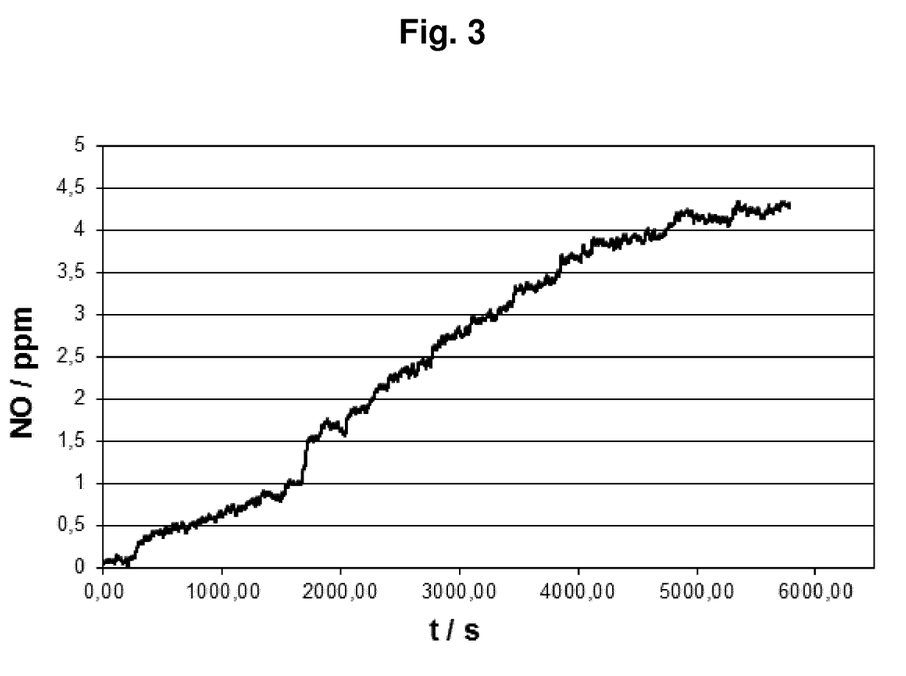
FIG. 3: shows the production of NO over a period of 100 min in a PLA membrane after the addition of water, sodium nitrite, and sodium-L-ascorbate. The plot shows the amount of NO produced in ppm over the time in seconds. For details, see Example 1.

The NO quantification by means of CLD is shown in FIG. 3. A continuous increase in the NO concentration was observed, whereby relevant values of 4 ppm were attained after approximately 75 minutes. Due to the presence of the antioxidant, ascorbate, highly pure NO was obtained as the reaction product through suppression of the production of N0$_2$.

The invention claimed is:
1. Skin or wound patch comprising
   (a) an oligomer and/or polymer that can produce an acidic environment by its hydrolysis, wherein the oligomer and/or polymer is formed as a fibre or as an enveloping layer of a core fibre, said fibre being the component of a knitted fabric, woven fabric, or non-woven fabric, wherein the polymer is a polyester selected from the group consisting of poly(D,L-lactide), poly(D-lactide), poly(L-lactide), poly(D,L-glycolide), poly(D-glycolide), poly(L-glycolide), poly(lactide-co-glycolide) (PLGA), polyhydroxybutyrate, poly(ε-caprolactone) (PCL), poly(ε-caprolactone-co-glycolide-co-D,L-lactide), and poly(p-dioxanone) (PPDO), poly(butylene succinate), poly(ethylene succinate) (PES), poly(butylene succinate-coadipate), poly(trimethylene carbonate), poly(propylene fumarate) (PPF), or copolymers thereof, and
   (b) an acid-activatable prodrug, wherein the acid activatable prodrug is embedded in a matrix comprising the oligomer and/or polymer or the acid activatable prodrug is coated or distributed on the oligomer and/or polymer formed as a fibre or an enveloping layer of a core fibre,
   wherein the acid-activatable prodrug is a pH-labile precursor of nitrogen monoxide and activatable in the skin or wound patch by the acid produced by hydrolysis upon placement on skin or wound areas of the body, and
   wherein the skin or wound patch is a sheet-shaped device for placement on skin areas of the body.

2. Skin or wound patch according to claim 1, characterised in that it contains an inductor or catalyst of oligomer or polymer hydrolysis.

3. Skin or wound patch according to claim 2, characterised in that the catalyst is an enzyme.

4. Skin or wound patch according to claim 1, characterised in that the fibre has a flat, oval, round, triangular, trilobate, Y-shaped, T-shaped, M-shaped, S-shaped, H-shaped or star-shaped cross-section.

5. Skin or wound patch according to claim 1 characterized in that the oligomer is a cyclic ester or a cyclic anhydride.

6. Skin or wound patch according to claim 1, characterised in that the acid activatable prodrug is present as a micro- or nano-particle.

7. Skin or wound patch according to claim 1, characterised in that it comprises a compound, which degrades or neutralises multiply oxidised nitrogen oxides, oxygen radical anions or hydroxyl radials.

8. Skin or wound patch according to claim 1, characterised in that it comprises the following:
   (a) a carrier layer; and
   (b) a layer containing
       i. the oligomer and/or polymer that can produce an acidic environment by its hydrolysis; and
       ii. the acid-activatable prodrug; and
   (c) optionally, a backing layer.

9. Skin or wound patch according to claim 1 for use during the treatment of diseases by placing or sticking the patch onto the area to be exposed to it.

10. Skin or wound patch according to claim 9 for use during the treatment of diseases by placing or sticking the patch onto the area to be exposed to it, characterised in that the treatment is selected from the group consisting of:
    (a) treatment of diabetic feet and wounds;
    (b) treatment of neuropathic pain;
    (c) treatment of varicose veins;
    (d) treatment of local superficial or deep-seated ischaemia and thrombopathic diseases of tissues;
    (e) treatment of acute and chronic inflammations of the skin;
    (f) treatment of skin allergies;
    (g) treatment of parasitic skin infections;
    (h) treatment of atopic dermatitis;
    (i) treatment of wound defects;
    (j) treatment of secondary healing infected wounds;
    (k) treatment of primary healing wounds;
    (l) treatment of extensive body regions for therapy of systemic diseases;
    (m) treatment of patients having skin grafts;
    (n) treatment of diabetic pain in the lower extremities (foot or leg); and
    (o) treatment of poorly perfused flap grafts.

11. Skin or wound patch according to claim 10, characterised in that it is used for treatment of chronic lower limb wounds of diabetics.

12. Method for the release of an active substance from the skin or wound patch of claim 1, comprising the following steps:
   (a) providing the skin or wound patch comprising the oligomer and/or polymer that can produce an acid environment by means of hydrolysis, and the acid-activatable prodrug;
   (b) contacting the polymer and/or oligomer to an inductor or catalyst such that the inductor or catalyst effects at least partial hydrolysis of the oligomer and/or polymer and such that an acidic environment is thus produced;
   (c) conversion of the acid-activatable prodrug into an active substance by the acidic environment from step (b);
   (d) release of the active substance from the skin or wound patch.

13. Skin or wound patch according to claim 3, wherein the enzyme is an esterase or lipase.

14. Skin or wound patch according to claim 1, wherein the polymer is a segmented block copolymer of polyether and polyester.

15. Skin or wound patch according to claim 5, wherein the oligomer is glycolide or lactide.

16. Skin or wound patch according to claim 1, wherein the pH-labile precursor is an inorganic nitrate or nitrite salt.

17. Skin or wound patch according to claim 7, wherein the compound is selected from the group consisting of ascorbic acid, vitamin E and derivatives thereof, thiols, and radical scavengers.

18. Skin or wound patch according to claim 10, wherein the treatment is selected from the group consisting of:
   (a) treatment of atopic dermatitis, wherein the atopic dermatitis is neurodermatitis, dermatomyositis, or pemphigus vulgaris;
   (b) treatment of wound defects, wherein the wound defects are chronic diabetic-neuropathic-ulcers, crural ulcers, or decubital wounds;
   (c) treatment of primary healing wounds, wherein the primary healing wounds are ablative lacerations or ablative abrasions; and
   (d) treatment of elevated blood pressure (hypertension) and related haemodynamic diseases.

19. Skin or wound patch according to claim 1, wherein said fibre is a component of a non-woven fabric.

* * * * *